United States Patent [19]

Roorda et al.

[11] Patent Number: 5,543,156
[45] Date of Patent: Aug. 6, 1996

[54] BIOERODIBLE DEVICES AND COMPOSITIONS FOR DIFFUSIONAL RELEASE OF AGENTS

[75] Inventors: Wouter E. Roorda, Newark; Fred P. Ehnow, San Carlos; Estela Basso, Santa Clara; Karly S. Wang, Newark; Sharon M. Fujita, Berkeley, all of Calif.

[73] Assignee: Alza Corporation, Palo Alto, Calif.

[21] Appl. No.: 184,770

[22] Filed: Jan. 21, 1994

Related U.S. Application Data

[63] Continuation of Ser. No. 984,388, Dec. 1, 1992, abandoned, which is a continuation of Ser. No. 709,862, Jun. 14, 1991, abandoned, which is a continuation-in-part of Ser. No. 641,222, Jan. 9, 1991, abandoned.

[51] Int. Cl.[6] .............................. A61K 9/10; A61K 9/14; A61K 9/22; A61K 9/70
[52] U.S. Cl. ...................... 424/484; 424/426; 424/428; 424/444; 424/486; 424/499; 424/501; 424/468
[58] Field of Search ..................... 424/484, 426, 424/428, 486, 444, 499, 501, 468

[56] References Cited

U.S. PATENT DOCUMENTS

| 4,070,347 | 1/1978 | Schmitt | 260/77.5 D |
|---|---|---|---|
| 4,093,709 | 6/1978 | Choi et al. | 424/19 |
| 4,122,158 | 10/1978 | Schmitt | 424/27 |
| 4,131,648 | 12/1978 | Choi et al. | 424/22 |
| 4,138,344 | 2/1979 | Choi et al. | 252/1 |
| 4,155,992 | 5/1979 | Schmitt | 424/19 |
| 4,180,646 | 12/1979 | Choi et al. | 528/153 |
| 4,432,964 | 2/1984 | Shell et al. | 424/427 |

OTHER PUBLICATIONS

Plastic Encyclopedia, vol. 46, pp. 62 to 70 (1969).

*Primary Examiner*—Edward J. Webman
*Attorney, Agent, or Firm*—Mary Ann Dillahunty; Richard T. Ito; Steven F. Stone

[57] ABSTRACT

The present invention is directed to erodible delivery devices and to the compositions comprising the devices. The devices comprise (a) a body formed of a bioerodible polymer or polymers together with a required excipient not generally considered to be a pore-former ("required excipient"), and (b) an active agent. The agent is released from the device at a controlled rate and in a therapeutically effective amount, with the rate being primarily independent of the erosion rate of the polymer. The rate of release of the active agent from the polymeric compositions of the present invention is significantly increased over the rate of release dependent on erosion of the polymer matrix. The invention makes possible the increased control over and improved reproducibility of the release profile of the agent from the polymer.

The invention is further directed to a method of delivering to an environment of use an active agent, which method comprises placing an appropriately sized and shaped delivery device of the above description in the environment of use.

29 Claims, 7 Drawing Sheets

5,543,156

BIOERODIBLE DEVICES AND COMPOSITIONS FOR DIFFUSIONAL RELEASE OF AGENTS

REFERENCE TO RELATED APPLICATION

This application is a continuation of application Ser. No. 07/984,388, filed Dec. 1, 1992, abandoned and benefit of the filing date of said earlier filed application is claimed number 35 U.S.C. §120, which is a continuation of application Ser. No. 07/709,862, filed Jun. 14, 1991, now abandoned, which is a continuation-in-part of application Ser. No. 07/641,222, filed Jan. 9, 1991, abandoned.

FIELD OF THE INVENTION

This invention pertains to bioerodible polymers and delivery devices made of bioerodible polymers. More particularly, this invention relates to bioerodible polymers useful for the delivery of an active agent, including those agents that do not normally diffuse from a polymer, the delivery being primarily independent of the erosion rate of the polymer.

BACKGROUND OF THE INVENTION

Bioerodible polymers are well known in the art, and the importance of delivery devices manufactured from such polymers has been long recognized. Such devices are valuable because they can contain a beneficial or otherwise active agent that, as the polymer erodes, is delivered at a controlled rate and in an effective amount to the environment of use.

One such family of polymers are the poly(orthoesters) disclosed in U.S. Pat. Nos. 4,070,347, 4,093,709, 4,122,158, 4,131,648, 4,138,344, and 4,155,992, for example. Other polymers are the poly(orthoesters) and poly(orthocarbonates) disclosed in U.S. Pat. No. 4,180,646. A third group of bioerodible polymers are the poly(lactic acids) and the poly(glycolic acids) and mixtures and copolymers thereof. All of these polymers have a controlled rate of erosion to innocuous products when in an aqueous or a biological environment.

Many active agents are released from these bioerodible polymers primarily by dissolution or erosion of the polymer. This is especially true of those agents which, because of high molecular weight or low solubility, for example, do not readily diffuse from a polymer matrix. However, release of beneficial agents by erosion may be undesirable or unaccceptable in many applications because the agent is not released or is released at an insufficient rate for a substantial period of time until erosion of the polymer has begun, and is thus unavailable to the environment for that extended "lag phase" period. Additionally, release through erosion of the polymer is a problem if it is desirable to have a rate of release of the agent which is different from the rate of erosion of the polymer, since release is normally dependent on the erosion rate of the polymer. Also, erosion of the polymer is not always continuous or predictable, so that the reproducibility of a release rate profile is often difficult.

Even where an agent is released from a bioerodible polymer by dissolution in and diffusion from the polymer, such diffusional release is often a slow process and not easily controlled. In general, the use of fillers in the polymeric matrix will slow this process. Additionally, the dissolution rate can be disturbed if the polymer loses its shape, which often happens with certain polymers when they are placed in a particular environment.

Therefore, it would be desirable to provide a means for controlling the delivery of an agent from a bioerodible polymer and to provide a reproducible release rate profile for the agent.

SUMMARY OF THE INVENTION

The present invention is directed to erodible delivery devices and to the compositions comprising the devices. The devices comprise (a) a body formed of a bioerodible polymer or polymers together with a required excipient not generally considered to be a pore-former ("required excipient"), and (b) an active agent. The agent is released from the device at a controlled rate and in a therapeutically effective amount, with the rate being primarily independent of the erosion rate of the polymer. The rate of release of the active agent from the polymeric compositions of the present invention is significantly increased over the rate of release from the polymer matrix without the required excipient, and the reproducibility of release from the compositions of the invention is substantially improved. The composition body of the device may optionally also include one or more pore-former materials.

The invention also concerns compositions comprising a bioerodible polymer or polymers and an excipient not generally considered to be a pore-former ("required excipient"). The composition may also optionally include one or more pore-former materials.

The invention is further directed to a method of delivering to an environment of use an active agent, including those that do not normally diffuse from a polymeric matrix, which method comprises placing an appropriately sized and shaped delivery device of the above description in the environment of use.

DETAILED DESCRIPTION OF THE INVENTION

Figure 1:
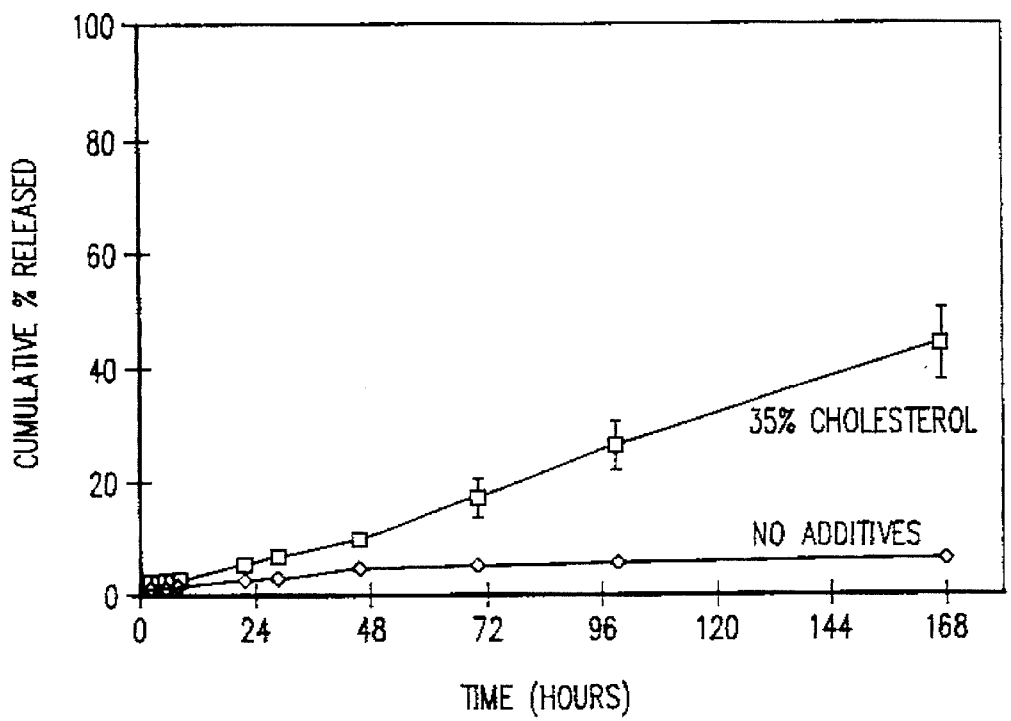
FIG. 1 shows graphically the cumulative percent release of lysozyme in vitro from a matrix according to the present invention and from a control matrix.

The active agent delivery devices of this invention provide several important advantages over previously known delivery systems. The devices provide for a bioerodible matrix system capable of providing a rate of release of an active agent from the system that is primarily independent of the rate of erosion of the polymer matrix. Also, the rate of release may be regulated by varying the amount of required excipient that is included in the matrix. Additionally, the active agent is released from the device of the invention at a rate that is significantly increased over the release rate of the agent from a bioerodible polymeric device that does not include the required excipient. Also, the release of the agent may occur during the lag phase of the bioerodible polymer. Thus, the invention makes possible the increased control over, as well as greater reproducibility of, the release profile of the agent from the polymer.

The release rate of an active agent from the system of the invention is primarily independent of the rate of erosion of the polymer matrix. What is meant herein by this is that, although there will likely be at least some erosion of the matrix during the useful life of the system so that a certain amount of the agent may be released as a result of such erosion, release of a significant amount, and usually substantially all of the agent can be achieved from the system of the invention without being dependent on the rate of erosion of the matrix.

As used herein, the terms an active agent or a drug which "does not normally diffuse" or "is normally non-diffusing" from a polymeric matrix refer to an active agent or a drug which under normal circumstances is incapable of being sufficiently released from a polymeric matrix by dissolution in the polymeric matrix and diffusion through and out of the matrix.

As used herein, the terms "therapeutically effective" amount or rate refer to the amount or rate of the active agent needed to effect the desired therapeutic result.

The term "matrix", as used herein, denotes a solid phase carrier within which the active agent can be dispersed. The carrier can be any desired shape, such as sphere, spheroid, cylinder, rod, sheet, and the like, or consistency, such as solid, malleable or deformable, flowable, and the like.

The terms "active agent" and "drug" are used interchangeably herein and refer to an agent, drug, compound or composition of matter which provides some therapeutic, often beneficial, effect.

The matrix material is biocompatible (e.g., it should not be toxic or otherwise cause adverse tissue reactions) and is bioerodible. The term "bioerodible" is used herein to mean materials which are degradable or erodible in vivo, either enzymatically or non-enzymatically, to produce biocompatible or non-toxic by-products, such as innocuous low molecular weight species. The by-products can be further metabolized or excreted via normal physiologic pathways.

The matrix material is also noncarcinogenic and causes no adverse immunological response.

Representative natural bioerodible materials include naturally occurring polymers such as collagen, cross-linked collagen, agar-agar, gelatin, cross-linked gelatin, and polysaccharides, for example.

Examples of bioerodible synthetic polymers include, but are not limited to, poly(lactic) acid and poly(glycolic acid) or their derivatives; copolymers of lactic acid and glycolic acid; polyamides; polyesters; poly(orthoesters); polycaprolactones; polyanhydrides; and polyvinylpyrrolidones. Mixtures and combinations of these may also be used.

One preferred type of bioerodible polymer comprises poly(orthoesters). Suitable poly(orthoester) polymers can be selected from those under the trademark Alzamer®. These polymers are disclosed in U.S. Pat. Nos. 4,070,347, 4,093,709, 4,122,158, 4,131,648, 4,138,344, and 4,155,992, for example, all of which are incorporated herein by reference. In a presently preferred embodiment, the polymers as used in this invention are based upon two Alzamer poly(orthoesters): 1) poly(2,2-dioxy-cis,trans-1,4-cyclohexane dimethylene tetrahydrofuran), which is a hard solid (glassy) polymer having the following structure (A):

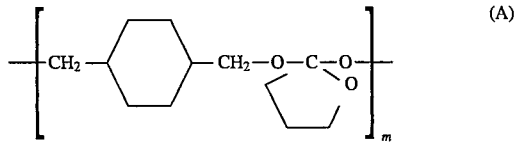

where m equals a number such that the molecular weight of the polymer (A) is within the range of 1,000 to 100,000; and 2) poly(2,2-dioxy-1,6-hexamethylene tetrahydrofuran), which is a viscous polymeric liquid having the following structure (B):

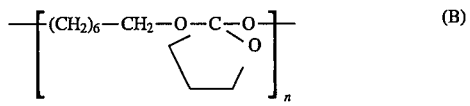

where n equals a number such that the molecular weight of the polymer (B) is within the range of 1,000 to 100,000.

Other orthoester polymers with similar physical properties can be substituted for the polymers noted above, and are disclosed in, for example, U.S. Pat. No. 4,180,646, which is incorporated herein by reference.

The bioerodible polymers useful in the present invention may also be chosen, for instance, from the poly(lactic acids) or the poly(glycolic acids) or copolymers of lactic acid and glycolic acid. Such polymers and copolymers are well known in the art and are well documented in the literature.

The polymeric matrix of the present invention may be selected from the group consisting of a homopolymer, physical mixtures of two or more polymers, and copolymers of two or more polymers. Methods for preparing these are known in the art or are described in the above-incorporated patents. In a presently preferred embodiment, the matrix is chosen from poly(orthoester) polymer (A) or a physical mixture of poly(orthoester) polymers (A) and (B).

The required excipient, which is a necessary component in the erodible polymeric matrix of the present invention, is an excipient that is not normally considered in the polymer arts to be a pore-former and yet provides a means for an active agent, including a normally non-diffusing agent, to be released from the matrix in a manner primarily independent of the erosion of the matrix and during the lag phase of the polymer. The required excipient can be chosen from, for example, hydrophobic compounds. Hydrophobic compounds which may be useful in the present invention include, but are not limited to, stearates such as calcium stearate, magnesium stearate, and aluminum stearate; phosphates such as calcium phosphate; myricyl cerotate; β-carotene; zeaxanthin; and cholesterol (3-hydroxy-5,6 -cholestene) and related compounds such as 3-amino-5,6-cholestene and other related analogs, 5,6-cholestene, and cholestane and related analogs such as 3-hydroxy-cholestane.

Cholesterol has been previously used as a structural component or a filler, but not as an agent to increase release rates or improve the reproducibility of release rates. For example, cholesterol can be a structural component of a liposome, providing a close-packed lipid structure to the liposome and slowing down the rate of release of the active agent. Cholesterol can be used as a filler in polymer matrices or can be added to matrices to modify the rate of controlled release of agent therefrom. In these prior uses, the presence of cholesterol was shown to either not affect the rate of release of agent or to slow down or decrease the rate of release of agent, with the release rate decreasing as the amount of cholesterol present is increased. This is consistent with the general belief in the polymer arts that fillers generally tend to slow the release of an agent.

Surprisingly, it has now been found that not only does the presence of cholesterol in the bioerodible matrix of the present invention allow an active agent to be released from the matrix at a rate that is primarily independent of the erosion rate of the matrix, but it also allows the agent to be released at a rate that is significantly greater than the release rate from such a matrix that does not include cholesterol. Additionally, and again surprisingly, the rate of release is increased as the amount of cholesterol in the polymeric matrix is increased.

It has also been found that the presence of cholesterol in the bioerodible matrix provides greatly improved reproducibility of the rate release profile of an active agent from the matrix.

The amount of the required excipient used for the present purpose will be dependent on several factors, such as the actual excipient used, the chosen polymeric component(s), the particular active agent to be released, the desired release rate and duration of release of the agent, and the body site at which the device is to be placed. Generally, the amount of required excipient is from about 1% to about 60% by weight (wt %) of the device. When cholesterol is used as the required excipient, the cholesterol may be present in an amount of from about 1 to about 50 wt % or higher, and preferably in an amount of from about 1 to about 35 wt %. As the amount of required excipient is increased in the matrix composition, the faster the active agent is released from the matrix system.

The present invention has been found to be useful for delivering a wide variety of active agents to the environment of use. In addition to those agents which are released from a bioerodible polymer by diffusion from a polymeric matrix, it has now surprisingly been found that agents which may be used in the present invention can include an agent that does not, under normal circumstances, diffuse from a polymeric matrix. Such an agent either cannot be released from the matrix at all or is released only as the matrix erodes and breaks apart. Such an agent may be normally non-diffusing for any one or more of a variety of reasons. For example, the agent may have too high a molecular weight and thus it becomes entrapped within the matrix structure, it may have a low solubility so that it cannot readily diffuse through the matrix, or it may have a low diffusion coefficient.

Exemplary agents that can be delivered according to this invention are those that are compatible with the polymeric matrix and with the required excipient and include, among others, biocides, sterilization agents, food supplements, nutrients, vitamins, sex sterilants, fertility inhibitors, and fertility promoters. They can include drugs that act on the peripheral nerves, adrenergic receptors, cholinergic receptors, nervous system, skeletal muscles, cardiovascular system, smooth muscles, blood circulatory system, synoptic sites, neuroeffector junctional sites, endocrine and hormone systems, immunological system, reproductive system, skeletal system, autocoid systems, alimentary and excretory systems, histamine system, and central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs, and synthetic analogs of these molecules.

Peptides and polypeptides which are suitable for use in this invention include, but are not limited to, insulin; glucagon; thyroid stimulating hormone; parathyroid and pituitary hormones; calcitonin; renin; prolactin; corticotrophin; thyrotropic hormone; follicle stimulating hormone; chorionic gonadotropin; gonadotropin releasing hormone; somatropin; somatotropin; oxytocin; vasopressin; prolactin; somatostatin; lypressin; pancreozymin; luteinizing hormone; interferons; interleukins; growth hormones such as human growth hormone, bovine growth hormone and porcine growth hormone; fertility inhibitors such as the prostaglandins; fertility promoters; growth factors; and human pancreas growth hormone releasing factor. Enzymes suitable for use include, but are not limited to, hydrolases, transferases, proteases, ligases, isomerases, lysases such as lysozyme, and the oxidoreductases such as esterases, phosphatases, glycosidases, and peptidases. Also capable of delivery from the device of this invention are bovine serum albumin, human serum albumin, proalbumin, unsecreted adrenocorticotrophin, thyroglobulin, soybean trypsin inhibitor, alkaline phosphatase, and catalase. Exemplary steroids useful in the invention include, but are not limited to, sterols; cardiac glycosides such as digitoxin, digoxin, and ouabain; corticosteroids such as hydrocortisone, hydrocorticosterone acetate, cortisone acetate and triamcinolone; and sex hormones such as testosterone, the estrogens, including 17β-estradiol and ethinyl estradiol, and the progestins, including progesterone, prednisolone, gestodene, levonorgestrel, ST-1435 and norethindrone. Local anesthetics useful in the invention include, but are not limited to, procaine, lidocaine, piperocaine, tetracaine, bupivacaine, dibucaine, mepivacaine, cocaine, benzocaine, their hydrochloride salts, and the like. Analgesics useful herein include, but are not limited to, morphine, codeine, meperidine, and nalorphine. Antibiotics include, but are not limited to, penicillins, cephalosporins, vancomycin, bacitracin, cycloserine, polymyxins, colistin, nystatin, tetracyclines, chloramphenicol, metronidazole, neomycin, streptomycin, kanamycin, erythromycin, and gentamicin. Antipyretics and anti-inflammatory agents include, but are not limited to, aspirin, indomethacin, salicylamide, naproxen, colchicine, ketoprofen, piroxicam, fenoprofen, diclofenac, and indoprofen. Ocular drugs include, but are not limited to, timolol, timolomaleate, pilocarpine, atropine, scopolamine and eserine salicylate. Muscle relaxants and antiparkinson agents include, but are not limited to, mephenesin, methocarbomal, levodopa/carbidope, and biperiden.

The active agent can be present in the invention in the various chemical and physical forms such as uncharged molecules, molecular complexes, and pharmacologically acceptable acid addition and base addition salts such as hydrochlorides, hydrobromides, sulfate, laurylate, palmitate, phosphate, nitrate, borate, acetate, maleate, tartrate, oleate and salicylate. For acidic compounds, salts of metals, amines or organic cations can be used. Derivatives of agents such as esters, ethers and amides can be used. An active agent can be used alone or mixed with other active agents.

The lists of active agents recited above are given only to illustrate the types of active agents which are suitable for use in practicing the invention, and are not intended to be exhaustive.

The amount of active agent employed in the delivery device will be that amount necessary to deliver a therapeutically effective amount of the agent to achieve the desired result at the site of application. In practice, this will vary depending upon the particular agent, the severity of the condition, and the desired effect, as well as the desired rate and duration of release.

In addition to the polymer, the required excipient and the active agent, the devices of this invention may also include, if desired, one or more diluents; vehicles; stabilizers such as potassium phosphate, sodium phosphate, sodium carbonate or magnesium hydroxide; dyes; inert fillers; pigments; and other components of polymeric matrix systems as are known in the art.

In one preferred embodiment, the device includes a hydrophilic pore-former such as lactose to provide an even greater release rate of agent from the matrix, when such increased release rate is desired. Generally, the hydrophilic pore-former is present in an amount of from about 1 wt % to about 50 wt %, preferably from about 5 wt % to about 35 wt %.

The devices of the invention can be manufactured by standard techniques. For example, the polymers with the required excipient and the agent mixed therewith can be extruded into filaments, spun into fibers, pressed into shaped articles, solvent film cast, doctor-bladed into thin films, coated by solvent evaporation, coated by using a fluidized bed, compression molded, transfer molded, formed into microparticles by coacervation or cryogrinding or solvent evaporation for example, and like methods of manufacture.

The devices can be a single matrix, a container with a reservoir therein, or a number of layers, for example. The devices can be made into various shapes such as flat, square, round, tubular, disc, ring, and the like. Presently preferred embodiments are films, rods, and particles. Also, the devices of the invention are sized, shaped and adapted for implantation, insertion, placement, depositing or spreading on the body, in the body, or in cavities and passageways of the body of an animal. Standard procedures for processing the polymer, the required excipient and the agent are known in the art or are described in *Plastic Encyclopedia*, Vol. 46, pp 62 to 70 (1969) and in the patents cited supra.

In the practice of the present invention, the device of the invention is placed in or on the environment of use. In the presently preferred embodiments, the environment of use is the body of an animal. Included in the term "animal" are humans, primates, mammals, domesticated or semi-domesticated animals (such as household, pet, and farm animals), laboratory animals (such as mice, rats and guinea pigs), birds, reptiles, fish, zoo animals, and the like. The devices may be placed on or in wounds, spread as a thin film, or injected as microparticles or as an implant into the body, for example.

The following examples are set forth as representative and illustrative of the spirit of the present invention. These examples are not to be construed as limiting the scope of the invention in any way.

EXAMPLE 1

The release profiles of the enzyme lysozyme (a high molecular weight peptide compound) from a matrix according to the present invention and from a prior art matrix were determined as follows.

Lysozyme, potassium phosphate and cholesterol were each dried and milled to a particle size of 5 microns. Fifty wt % of the polymer poly(2,2-dioxy-cis,trans-1,4-cyclohexane dimethylene tetrahydrofuran) (polymer (A)) having a molecular weight of 28,000, 35 wt % of cholesterol and 5 wt % of potassium phosphate were hand-mixed together at 110°–120° C. for 10 min. Lysozyme (10 wt %) was added, and mixing was continued for 5 min. The mixture was then placed in a CSI miniextruder and mixing was continued for 5 min. at 90° C. It was then melt-pressed at 90° C. into sheets which were die cut into 1×1 cm squares, 0.25 mm thick.

Polymeric squares not containing cholesterol (the control) were prepared in the same manner and had a composition of 85 wt % polymer (A), 10 wt % lysozyme and 5 wt % potassium phosphate.

The squares were placed between two pieces of dialysis tubing and clamped with two concentric teflon rings. Six squares were tested from each formulation. Each square device held by the teflon rings was immersed in release rate media (phosphate buffer, pH 7.2), and the amount of lysozyme released into the buffer was measured at selected intervals. After each measurement, the device was placed in fresh media.

The cumulative percent release of the lysozyme from each of the two formulations is presented in FIG. 1 and shows an increasing release of the enzyme from the matrix containing the cholesterol and almost no release of the enzyme from the noncholesterol-containing matrix over a period of 7 days.

EXAMPLE 2

Following the procedures of Example 1, square devices were made with the following composition: 50 wt % polymer (A) (Mw=28,000), 5 wt % potassium phosphate, 10 wt % lysozyme, 20 wt % cholesterol and 15 wt % lactose. The release of lysozyme was determined, in comparison with the release from control devices (of the same composition as the controls in Example 1).

Figure 2:
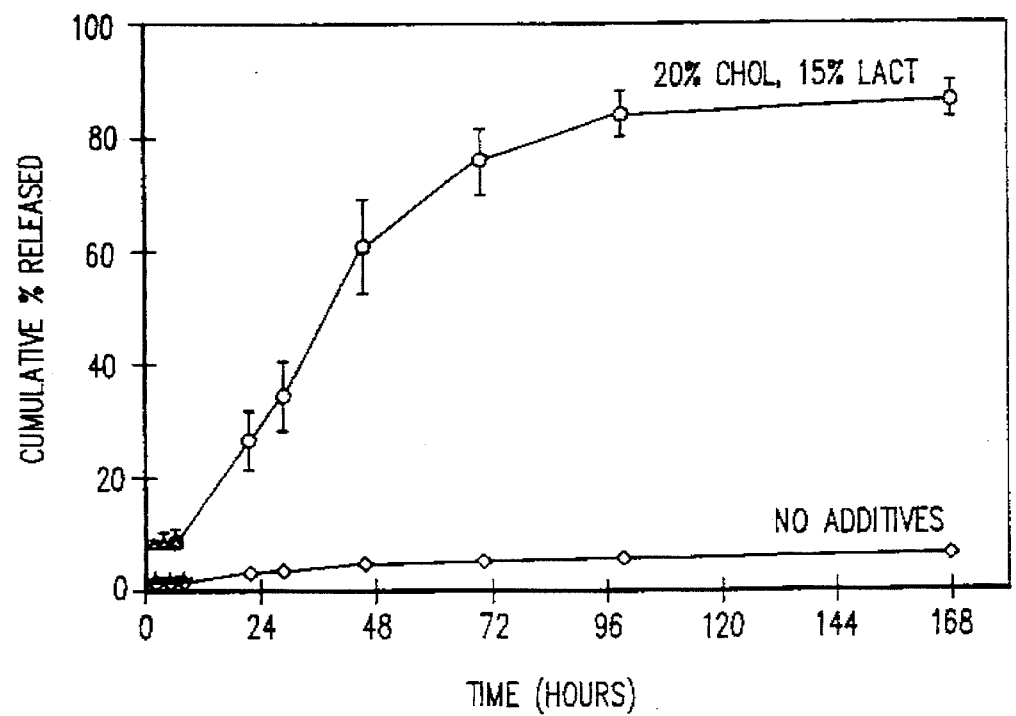
FIG. 2 shows graphically the cumulative percent release of lysozyme in vitro from a matrix according to the present invention which includes, in addition, lactose, and from a control matrix.

The cumulative percent release of lysozyme (from six devices each) was determined and is presented in FIG. 2.

EXAMPLE 3

Different shaped devices (sheets and rods) were prepared and tested for lysozyme release, both in vivo and in vitro.

Preparation of the additives and mixing of the ingredients were carried out following the procedures of Example 1. Two formulations, listed in Table A below, were prepared.

TABLE A

| Composition (wt %) | Formulation | |
|---|---|---|
| | 1 | 2 |
| Polymer (A) | 50 | 70 |
| Lysozyme | 10 | 10 |
| Potassium phosphate | 5 | 5 |
| Cholesterol | 35 | 15 |

Sheets were prepared from each of Formulations 1 and 2 by melting-pressing the mixture in a Carver press into 0.25 mm×1 cm×1 cm slabs. Rods from each formulation were prepared by extruding the mixture into 2 mm diameter×1 cm length rods, using a miniextruder. Weight of each sheet or rod was approximately 30 mg.

To determine the release rate of lysozyme from the devices in vitro, each sheet or rod was placed in dacron mesh and held in release media, following the procedures in Example 1.

To determine the release rate in vivo, both sheets and rods were implanted subcutaneously in rats. For each time point, three devices of each formulation and shape were implanted. Devices were explanted from the rats at selected time points, and the residual lysozyme remaining in each device was analyzed by HPLC after hydrolyzing the polymer (by heat for 1 hour at 50° C. with 1% HCl).

Figure 3A:
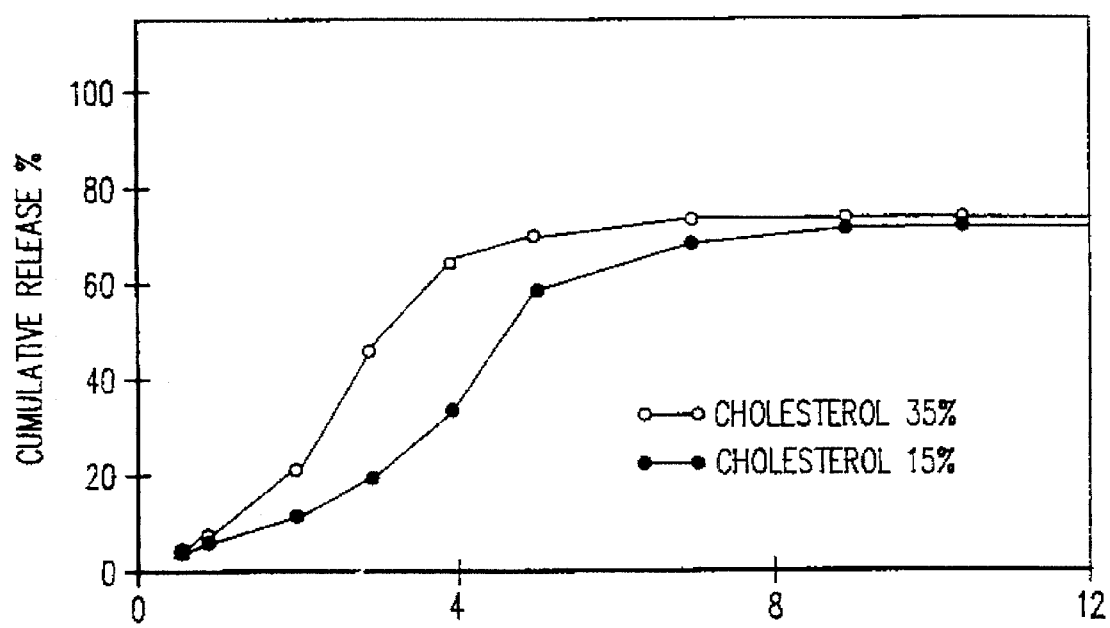
FIG. 3 shows graphically the cumulative percent release of lysozyme in vitro from devices of the present invention, the devices shaped either as sheets (FIG. 3a) or as rods (FIG. 3b).
Figure 3B:
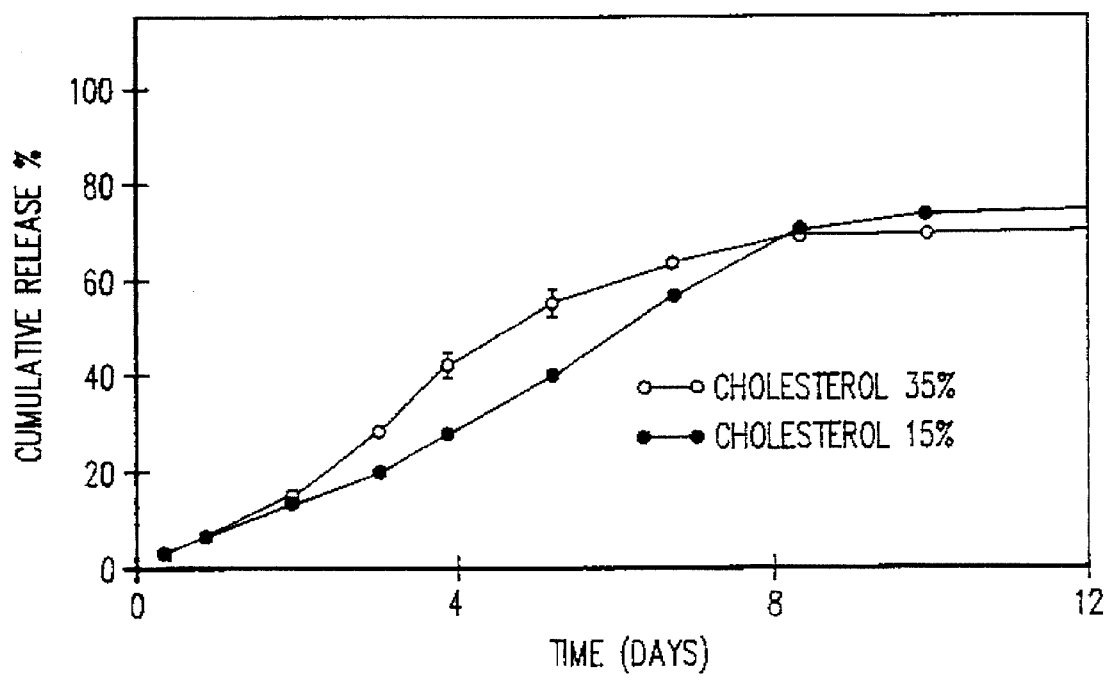

The cumulative percent release of lysozyme in vitro from each of the two formulations is presented in FIG. 3. FIG. 3(a) shows the release from the sheets and FIG. 3(b) shows the release from the rods. The devices containing 35 wt % cholesterol released the enzyme more quickly than those containing 15 wt % cholesterol, and most of the lysozyme was released from formulation 1 before 5 days, while formulation 2 released the lysozyme over about 9.5 days.

The cumulative release of lysozyme in vivo was greater in all cases than the cumulative release in vitro, but in each case the release in vivo proportionally followed basically the same release rate profile as those of the in vitro release.

EXAMPLE 4

To determine the release of lidocaine (a low molecular weight diffusional compound) from matrices of the invention, devices were prepared following the procedures of Example 1 and having the compositions indicated under Table B below.

TABLE B

| Composition (wt %) | Formulation | | | |
|---|---|---|---|---|
| | a | b | c | d |
| Polymer (A) | 70 | 60 | 45 | 20 |
| Lidocaine | 30 | 30 | 30 | 30 |
| Cholesterol | 0 | 10 | 25 | 50 |

The matrices were each formed into a film of 0.25 mm thickness and cut into 1 cm×1 cm squares. Each square was placed into 10.0 ml of pH 7.2 phosphate buffer release media and held at 37° C. in a shaking water bath. The release of the lidocaine from the matrices into the media was measured at time intervals over a period of 360 hours following the procedures of Example 1.

Figure 4:
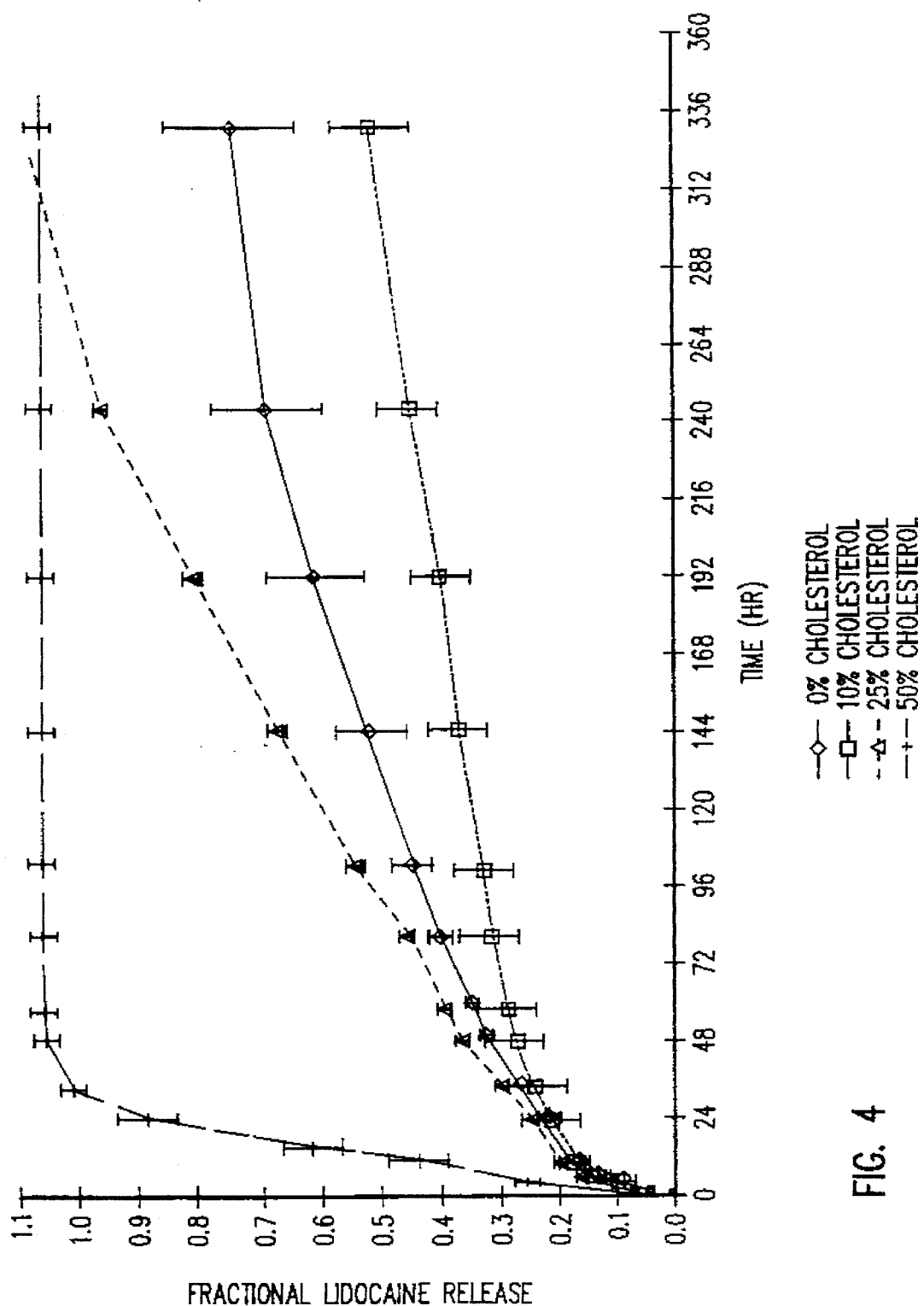
FIG. 4 shows graphically the release rates of lidocaine from devices of the present invention containing varying amounts of cholesterol.

The results are presented in FIG. 4 and show that cholesterol can be used to vary the release profile of a low molecular weight drug such as lidocaine. They also show that the release of lidocaine increased as the amount of cholesterol in the matrix was increased above 10 wt %.

EXAMPLE 5

Figure 5:
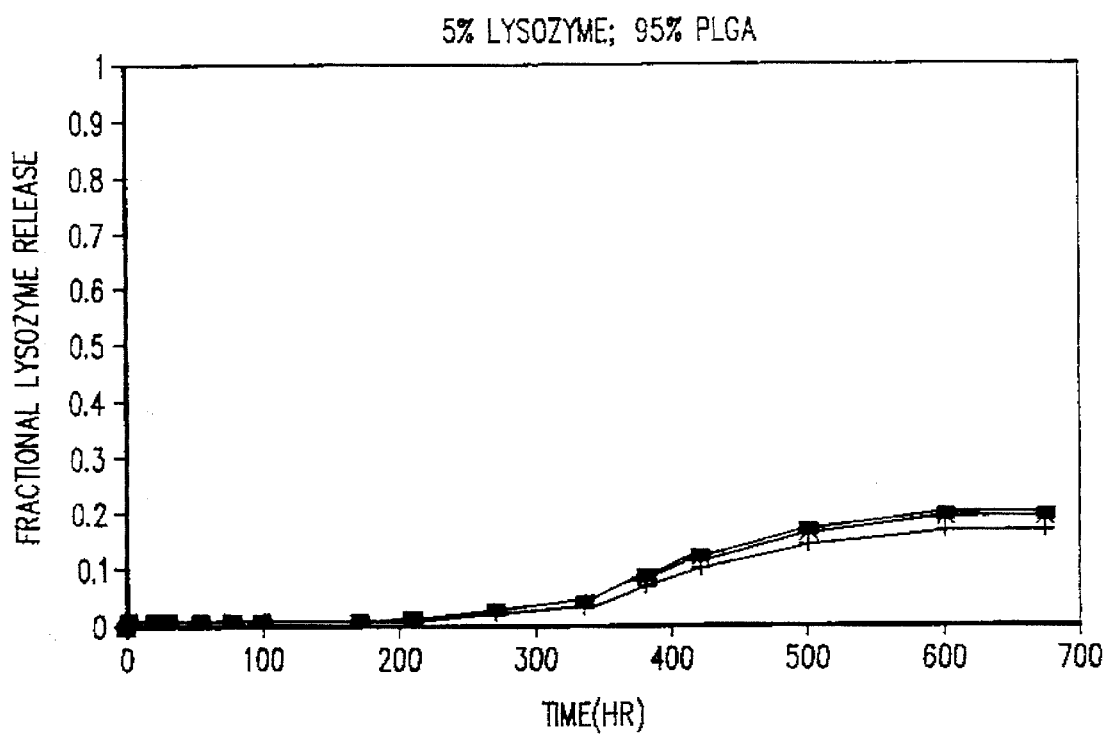
FIG. 5 shows graphically the release rates of lysozyme from control devices that do not contain a required excipient.
Figure 6:
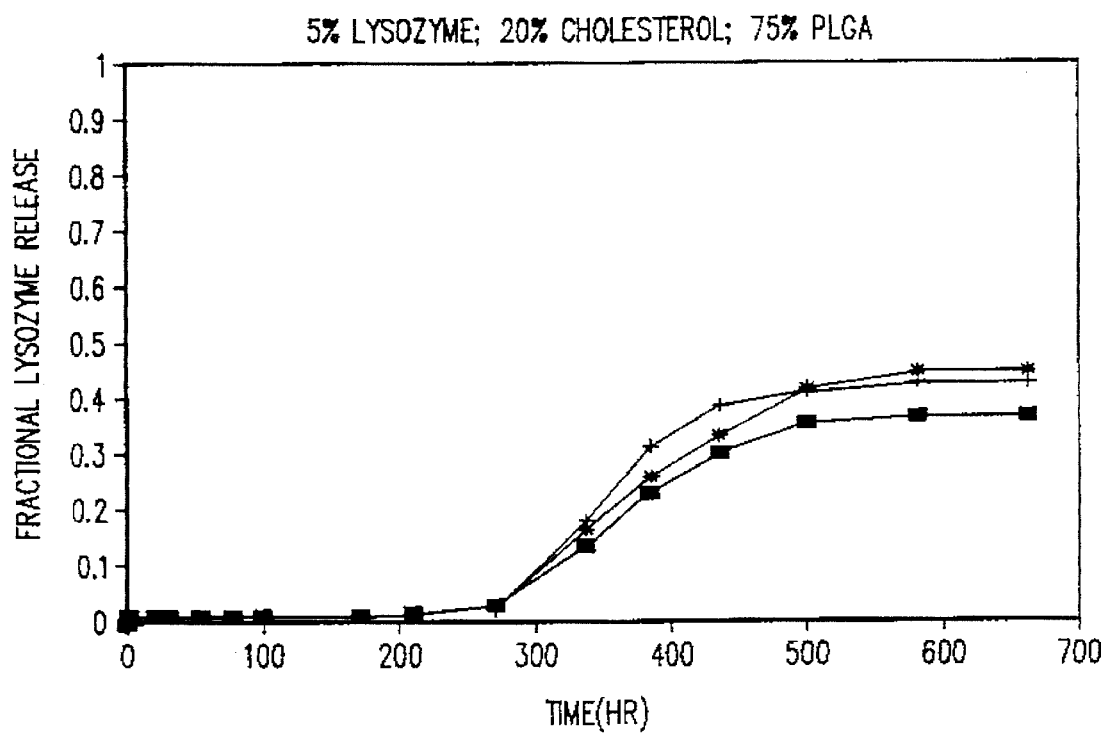
FIG. 6 shows graphically the release rates of lysozyme from devices of the present invention containing cholesterol.
Figure 7:
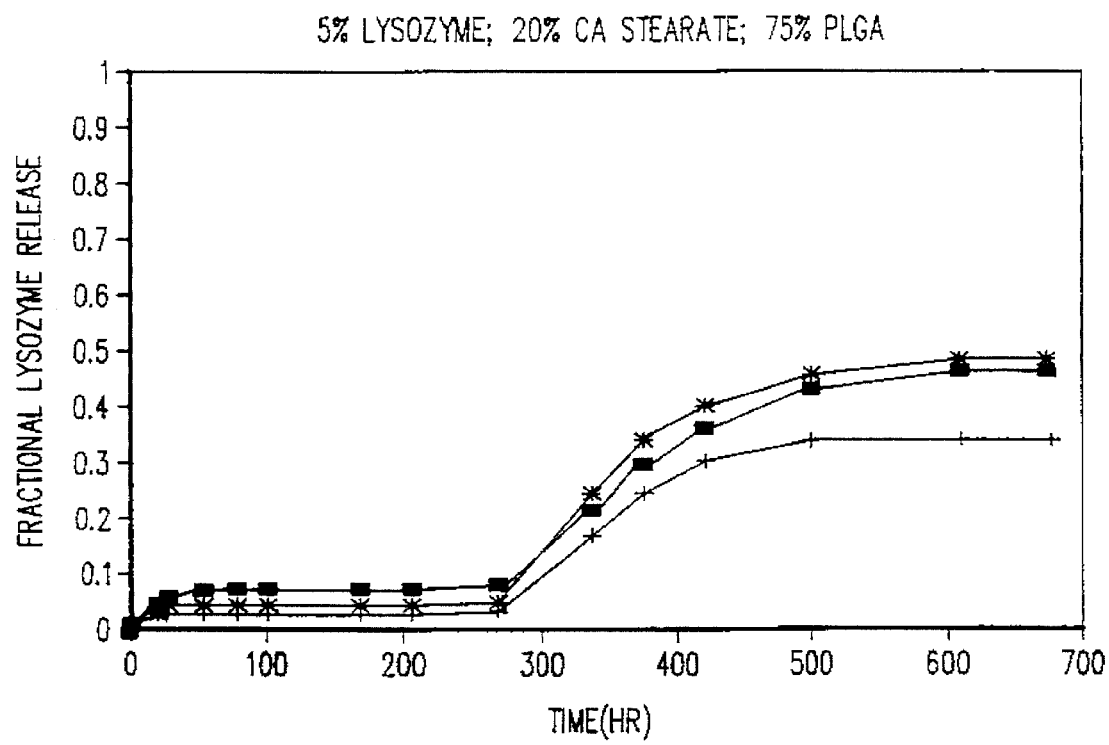
FIG. 7 shows graphically the release rates of lysozyme from devices of the present invention containing calcium stearate.
Figure 8:
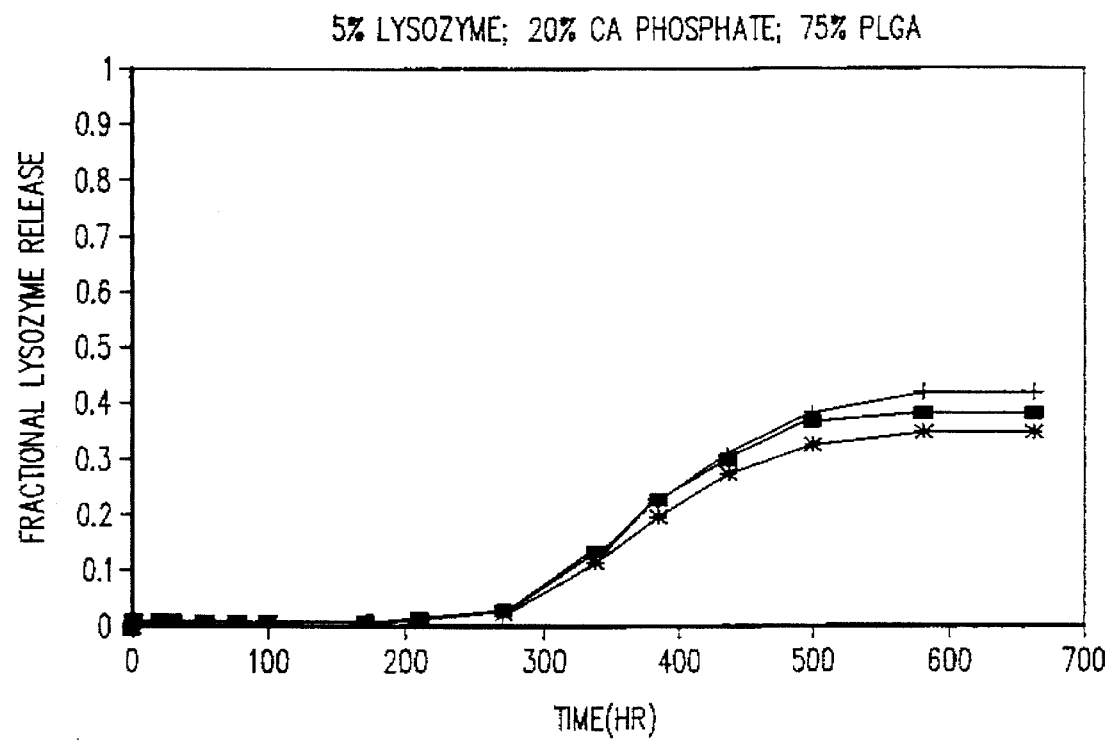
FIG. 8 shows graphically the release rates of lysozyme from devices of the present invention containing calcium phosphate.

Following the procedures of Example 1, 1×1 cm square devices, 0.5 mm thick, were made having the following composition: 75 wt % poly(lactic-glycolic) copolymer ("PLGA") (Resomer® 503, Boehringer Ingelheim; 50:50 lactic acid:glycolic acid; intrinsic viscosity 0.4±10%; approx. 30,000 MW), 5 wt % lysozyme and 20 wt % hydrophobic excipient. The hydrophobic excipients tested were cholesterol, calcium stearate and calcium phosphate. Control devices were composed of 95 wt % PLGA (Resomer 503) and 5 wt % lysozyme. Certain of the devices were irradiated (β-irradiation) at 2.5 megarad. The in vitro release of lysozyme through human cadaver skin was determined (n=3 devices) and the percent release of the various devices is presented in FIGS. 5 (control), 6 (cholesterol), 7 (calcium stearate) and 8 (calcium phosphate). The devices shown in the Figures had been irradiated; the results with non-irradiated devices were substantially similar.

EXAMPLE 6

Figure 9:
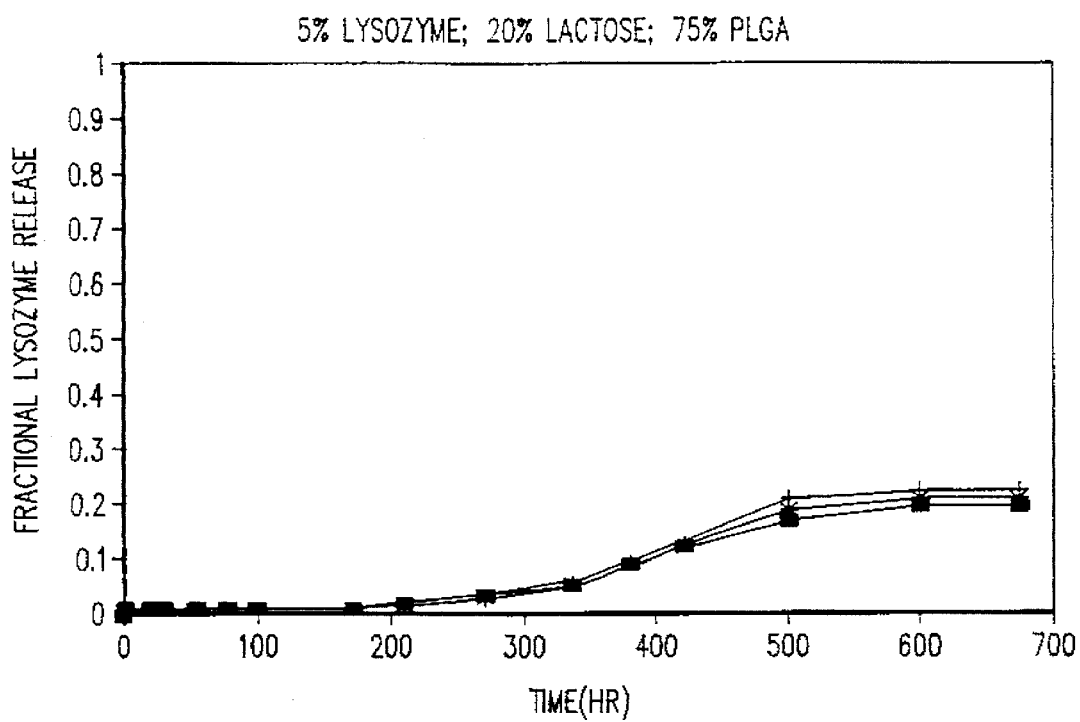
FIG. 9 shows graphically the release rates of lysozyme from control devices that do not contain a required excipient.
Figure 10:
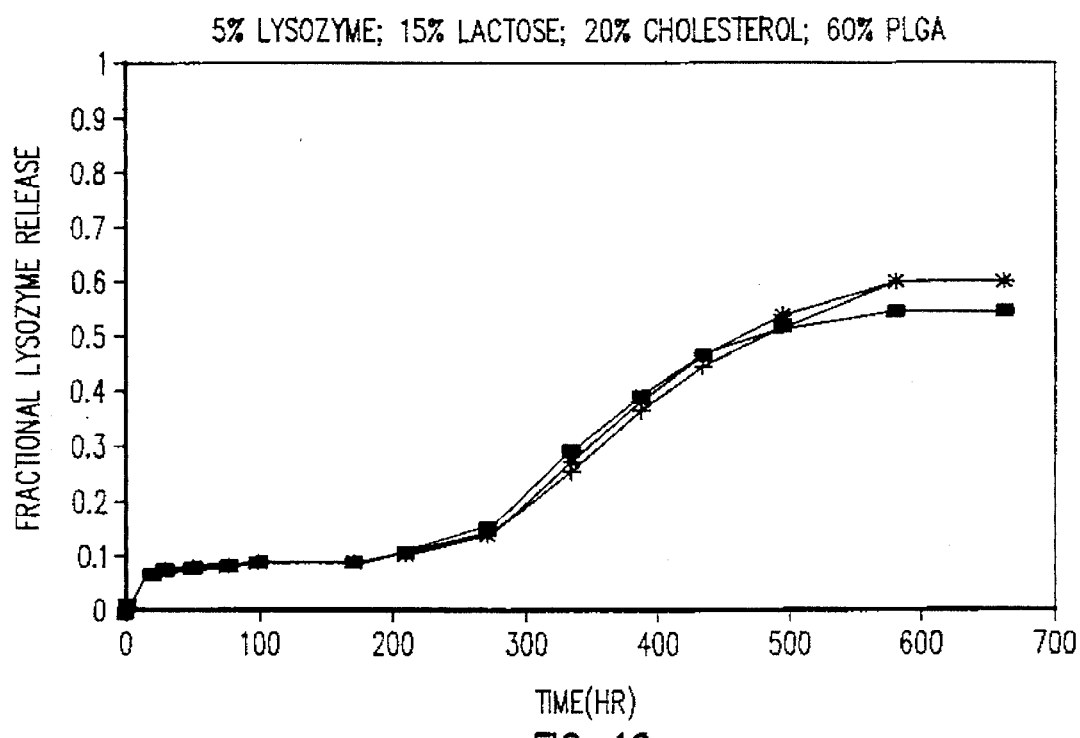
FIG. 10 shows graphically the release rates of lysozyme from devices of the present invention containing cholesterol.
Figure 11:
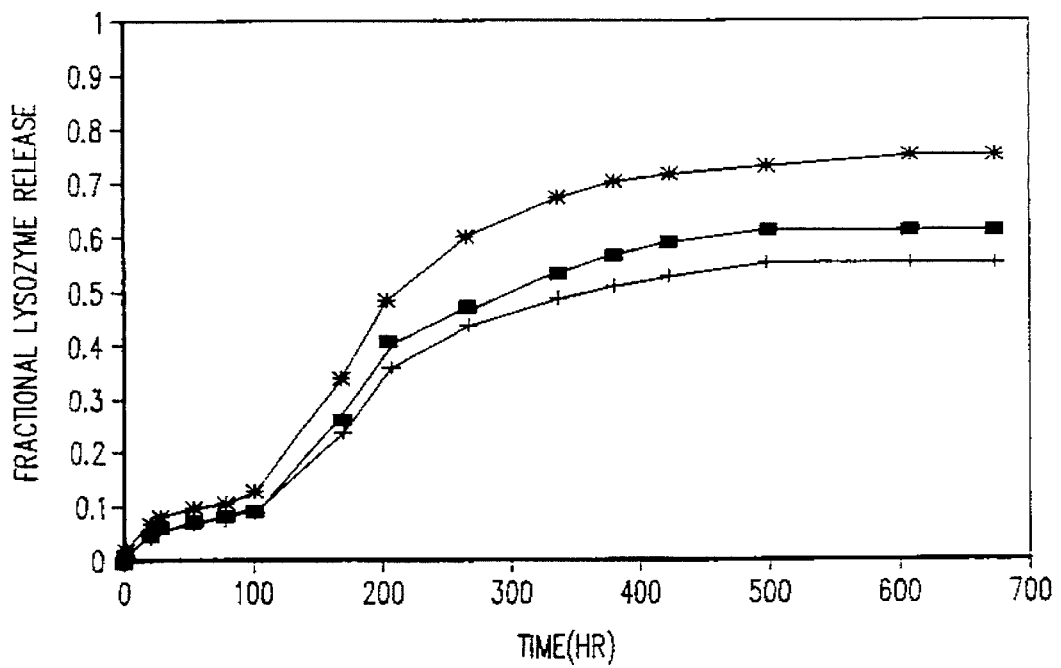
FIG. 11 shows graphically the release rates of lysozyme from devices of the present invention containing calcium stearate.
Figure 12:
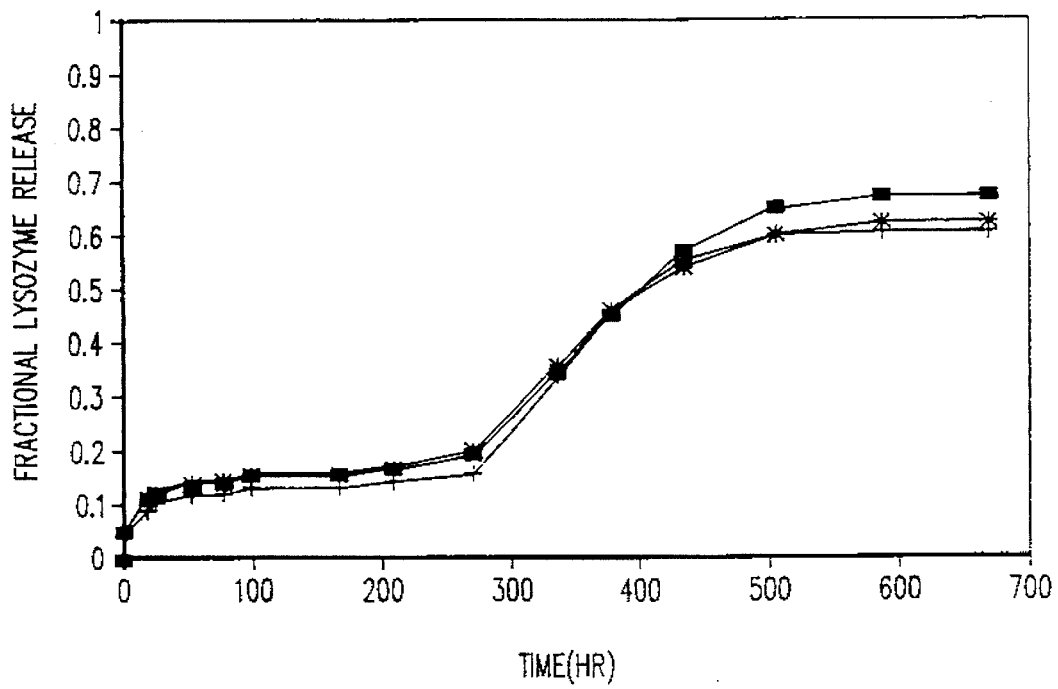
FIG. 12 shows graphically the release rates of lysozyme from devices of the present invention containing calcium phosphate.

Following the procedures of Example 1, 1×1 cm square devices, 0.5 mm thick, were made having the following composition: 60 wt % poly(lactic-glycolic) copolymer ("PLGA") (Resomerl 503, Boehringer Ingelheim; 50:50 lactic acid:glycolic acid; intrinsic viscosity 0.4±10%; approx. 30,000 MW), 5 wt % lysozyme, 15 wt % lactose and 20 wt % hydrophobic excipient. The hydrophobic excipients tested were cholesterol, calcium stearate and calcium phosphate. Control devices were composed of 75 wt % PLGA (Resomer® 503), 5 wt % lysozyme and 20 wt % lactose. Certain of the devices were irradiated (β-irradiation) at 2.5 megarad. The in vitro release of lysozyme through human cadaver skin was determined (n=3 devices) and the percent release of the various devices is presented in FIGS. 9 (control), 10 (cholesterol), 11 (calcium stearate) and 12 (calcium phosphate). The devices shown in the Figures had been irradiated; the results with non-irradiated devices were substantially similar.

What is claimed is:

1. A device for delivering a pharmaceutically active agent to an animal at a controlled rate over a prolonged period of time, wherein the device comprises:
   (a) a body, shaped, sized and adapted for delivering a pharmaceutically active agent to the animal, the body comprises:
      (i) 29–86 wt % of bioerodible polymer, a copolymer of bioerodible polymers, or a mixture of bioerodible polymers, and
      (ii) 14–71 wt % of a hydrophobic compound, the hydrophobic compound being selected from the group consisting of stearates, phosphates, β-carotene, zeazanthin, cholesterol and 5,6-cholestene; and
   (b) a therapeutically effective amount of the agent to be delivered; wherein the body is characterized by the delivery rate of the agent to be delivered from the matrix being greater when the body comprises (i) and (ii) than when the body comprises (i).

2. A device according to claim 1 wherein the hydrophobic compound is cholesterol and the bioerodible polymer is a poly(orthoester) polymer, a poly(lactic acid) polymer, a poly(glycolic acid) polymer or a copolymer of lactic acid and glycolic acid.

3. A device according to claim 2 wherein the polymeric matrix further comprises 5–35 wt % lactose.

4. A device according to claim 1 wherein the hydrophobic compound is cholesterol and the bioerodible polymer is a poly(orthoester) polymer.

5. A device according to claim 1 wherein the hydrophobic compound is cholesterol, calcium stearate or calcium phosphate and the bioerodible polymer is a copolymer of lactic acid and glycolic acid.

6. A composition of matter useful as an erodible matrix material for delivering a pharmaceutically active agent the composition of matter comprising:
   (a) 29–86 wt % bioerodible polymer, a copolymer of bioerodible polymers, or a mixture of bioerodible polymers; and (b) 14–71 wt % of a hydrophobic compound, the hydrophobic compound being selected from the group consisting of stearates, phosphates, β-carotene, zeazanthin, and cholesterol wherein the matrix material is charactered by a delivery rate of the agent to be delivered from the matrix being greater when the matrix comprises (i) and (ii) than when the matrix comprises (i).

7. A composition according to claim 6 wherein the hydrophobic compound is cholesterol and the bioerodible polymer is a poly(orthoester) polymer, a poly(lactic acid) polymer, a poly(glycolic acid) polymer or a copolymer of lactic acid and glycolic acid.

8. A composition according to claim 6 wherein the hydrophobic compound is cholesterol and the bioerodible polymer is a poly(orthoester) polymer.

9. A composition according to claim 6 wherein the hydrophobic compound is cholesterol, calcium stearate or calcium phosphate and the bioerodible polymer is a copolymer of lactic acid and glycolic acid.

10. A method for delivering a pharmaceutically active agent to an animal at a controlled rate and over a prolonged period of time, which method comprises placing a delivery device in the animal, wherein the delivery device is comprised of:
    (a) a shaped body, sized and adapted for delivering a pharmaceutically active agent to the animal, the body formed of an erodible, release rate-controlling matrix material, where the matrix material comprises:
        (i) 29–86 wt % bioerodible polymer, a copolymer of bioerodible polymers, or a mixture of bioerodible polymers, and
        (ii) 14–71 wt % of a hydrophobic compound, the hydrophobic compound being selected from the group consisting of stearates, phosphates, β-carotene, zeazanthin, cholesterol, and 5,6-cholestene; and
    (b) A therapeutic amount of the agent to be delivered, wherein the delivery rate of the agent being greater when the matrix comprises (i) and (ii) than when the matrix comprises (i).

11. A method according to claim 10 wherein the hydrophobic compound is cholesterol and the bioerodible polymer is a poly(orthoester) polymer, a poly(lactic acid) polymer, a poly(glycolic acid) polymer or a copolymer of lactic acid and glycolic acid.

12. A method according to claim 11 wherein the polymeric matrix further comprises 5–35 wt % lactose.

13. A method according to claim 10 wherein the hydrophobic compound is cholesterol and the bioerodible polymer is a poly(orthoester) polymer.

14. A method according to claim 10 wherein the hydrophobic compound is cholesterol, calcium stearate or calcium phosphate and the bioerodible polymer is a copolymer of lactic acid and glycolic acid.

15. A method for increasing the rate of release of a pharmaceutically active agent to an animal from a bioerodible polymeric matrix over time and primarily independent of the rate of erosion of the polymeric matrix, which method comprises:
    (a) mixing a polymeric matrix, comprising
        (i) 29–86 wt % bioerodible polymer, a copolymer of bioerodible polymers, or a mixture of bioerodible polymers, with
        (ii) 14–71 wt % of a hydrophobic compound, the hydrophobic compound being selected from the group consisting of stearates, phosphates, β-carotene, zeazanthin, cholesterol and 5,6-cholestene;
    (b) incorporating a therapeutically effective amount of the agent into the polymeric matrix wherein the matrix is characterized by the delivery rate of the agent to be delivered from the matrix being greater when the matrix comprises (i) and (ii) than when the matrix comprises (i).

16. A method according to claim 15 wherein the hydrophobic compound is cholesterol and the bioerodible polymer is a poly(orthoester) polymer, a poly(lactic acid) polymer, a poly(glycolic acid) polymer or a copolymer of lactic acid and glycolic acid.

17. A method according to claim 16 wherein the polymeric matrix further comprises 5–35 wt % lactose.

18. A method according to claim 15 wherein the hydrophobic compound is cholesterol and the bioerodible polymer is a poly(orthoester) polymer.

19. A method according to claim 15 wherein the hydrophobic compound is cholesterol, calcium stearate or calcium phosphate and the bioerodible polymer is a copolymer of lactic acid and glycolic acid.

20. A method for increasing the rate of release of a pharmaceutically active agent to an animal from a bioerodible polymeric matrix over time, which method comprises:
    (a) incorporating the agent, in a therapeutically effective amount, into the polymeric matrix, which matrix is comprised of:
        (i) 29–86 wt % bioerodible polymer, a copolymer of bioerodible polymers, or a mixture of bioerodible polymers, and
        (ii) 14–71 wt % of a hydrophobic compound, the hydrophobic compound being selected from the group consisting of stearates, phosphates, β-carotene, zeazanthin, cholesterol, or 5,6-cholestene; and
    (b) placing the polymeric matrix containing the agent in the animal wherein the matrix is characterized by the delivery rate of the agent to be delivered from the matrix being greater when the matrix comprises (i) and (ii) than when the matrix comprises (i).

21. A method according to claim 20 wherein the hydrophobic compound is cholesterol and the bioerodible polymer is a poly(orthoester) polymer, a poly(lactic acid) polymer, a poly(glycolic acid) polymer or a copolymer of lactic acid and glycolic acid.

22. A method according to claim 21 wherein the polymeric matrix further comprises 5–35 wt % lactose.

23. A method according to claim 20 wherein the hydrophobic compound is cholesterol and the bioerodible polymer is a poly(orthoester) polymer.

24. A method according to claim 20 wherein the hydrophobic acid is cholesterol, calcium stearate or calcium phosphate and the bioerodible polymer is a copolymer of lactic acid and glycolic acid.

25. A method for providing improved reproducibility of the release profile of a pharmaceutically active agent to an animal from a bioerodible polymeric matrix over time, where the release profile of the agent is primarily independent of the rate of erosion of the polymeric matrix, which method comprises:
    (a) incorporating the agent, in a therapeutically effective amount, into the polymeric matrix, which matrix is comprised of:
        (i) 29–86 wt % bioerodible polymer, a copolymer of bioerodible polymers, or a mixture of bioerodible polymers, and
        (ii) 14–71 wt % of a hydrophobic compound, the hydrophobic compound being selected from the group consisting of stearates, phosphates, β-carotene, zeazanthin, cholesterol, or 5,6-cholestene; and (b) placing the polymeric matrix containing the agent in the animal wherein the matrix is characterized by the delivery rate of the agent to be delivered from the matrix being greater when the matrix comprises (i) and (ii) than when the matrix comprises (i).

26. A method according to claim 25 wherein the hydrophobic compound is cholesterol and the bioerodible polymer is a poly(orthoester) polymer, a poly(lactic acid) polymer, a poly(glycolic acid) polymer or a copolymer of lactic acid and glycolic acid.

27. A method according to claim 26 wherein the polymeric matrix further comprises 5–35 wt % lactose.

28. A method according to claim 25 wherein the hydrophobic compound is cholesterol and the bioerodible polymer is a poly(orthoester) polymer.

29. A method according to claim 25 wherein the hydrophobic acid is cholesterol, calcium stearate or calcium phosphate and the bioerodible polymer is a copolymer of lactic acid and glycolic acid.

* * * * *